United States Patent [19]

Zaneveld et al.

[11] Patent Number: 4,512,342
[45] Date of Patent: Apr. 23, 1985

[54] DEVICE AND METHOD FOR REVERSIBLY OCCLUDING A BODY DUCT

[75] Inventors: Lourens J. D. Zaneveld, 900 N. Lake Shore Dr., Chicago, Ill. 60611; James W. P. Burns, 146 S. Elgin Ave., Forest Park, Ill. 60130

[73] Assignees: Lourens J. D. Zaneveld; James W. P. Burns, both of Chicago, Ill.

[21] Appl. No.: 368,275

[22] Filed: Apr. 14, 1982

[51] Int. Cl.³ ............................................. A61B 19/00
[52] U.S. Cl. .............................. 128/303 R; 128/1 R; 128/325; 3/1
[58] Field of Search ................... 128/1 R, 303 R, 325; 3/1

[56] References Cited

U.S. PATENT DOCUMENTS

| | | | |
|---|---|---|---|
| 3,589,355 | 6/1971 | Lee | 128/1 R |
| 3,678,129 | 8/1972 | Nuwayser | |
| 3,820,528 | 6/1974 | Rogers | |
| 3,858,571 | 1/1975 | Rudolph | 128/1 R |
| 3,882,845 | 5/1975 | Bucalo | 128/1 R |
| 3,990,434 | 11/1976 | Free | |
| 4,168,708 | 9/1979 | Lepley, Jr. et al. | 128/1 R |
| 4,305,395 | 12/1981 | Martinez | 3/1 A |

OTHER PUBLICATIONS

*Reversal of Sterilization*—PARFR Series on Fertility Regulation, Dec. 4-6, 1977, FIG. 9-2, p. 88.

*Primary Examiner*—Richard J. Apley
*Assistant Examiner*—Gregory Beaucage
*Attorney, Agent, or Firm*—Emrich & Dithmar

[57] ABSTRACT

A device and method for reversibly occluding a body duct, such as the vas deferens, to prevent fluid flow therethrough. The device comprises two spaced flexible plugs connected to each other by a flexible connecting member, such as a suture or other filament. The plugs are of size so as to be snugly received by the lumen of the body duct at implantation without exerting excessive pressure therein. The device is preferably implanted in the duct by insertion of each plug through a respective puncture hole in the wall of the duct, with a portion of the connecting member being retained externally of the duct to prevent migration of the plugs.

18 Claims, 9 Drawing Figures

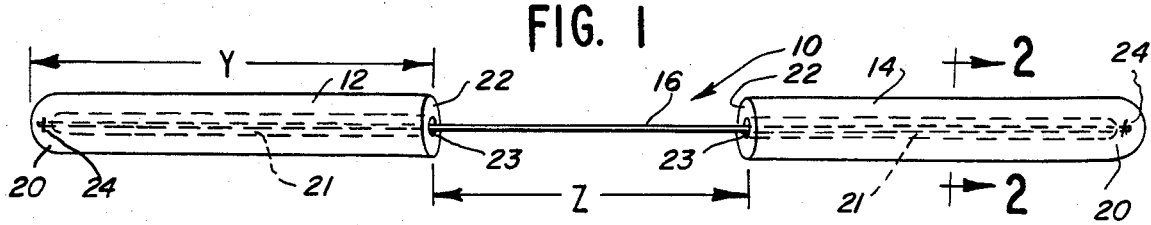
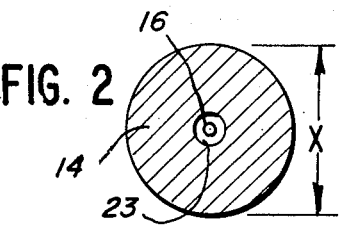
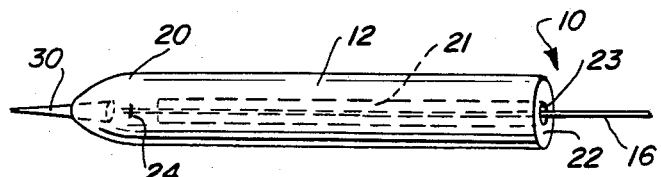
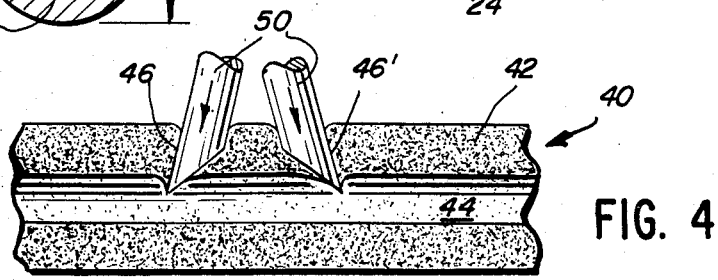
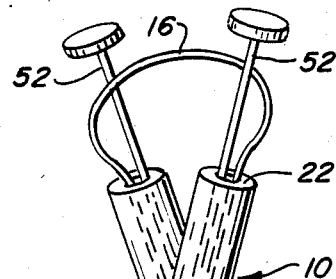
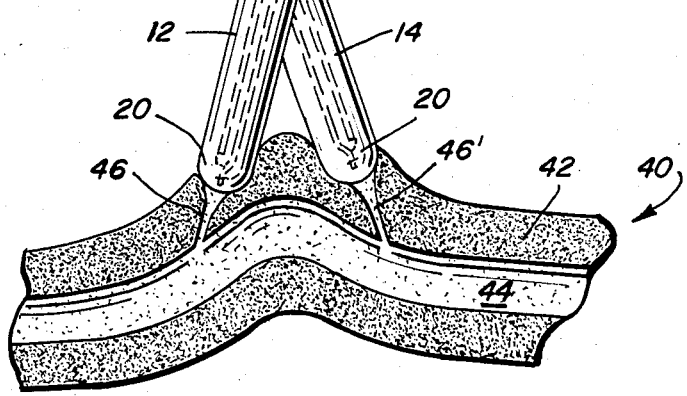
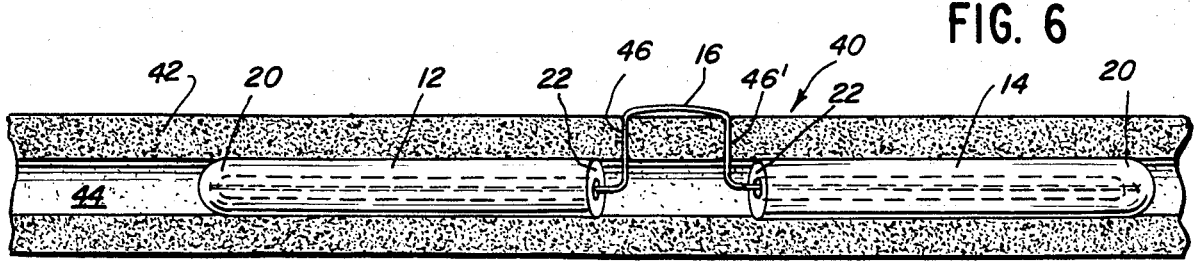

DEVICE AND METHOD FOR REVERSIBLY OCCLUDING A BODY DUCT

ACKNOWLEDGEMENT OF GOVERNMENT RIGHTS

The Government has rights in this invention pursuant to Contract No. AID/DSPE-C-0035 awarded by the Agency for International Development.

BACKGROUND OF THE INVENTION

1. Field of the Invention

This invention relates generally to a device and method for occluding a body duct and, more specifically, this invention relates to a device and method for reversibly occluding such a duct for preventing passage of duct contents therethrough. The invention is especially applicable to reversible occlusion of the vas deferens in order to achieve male sterilization.

2. Description of the Prior Art

A number of methods are available to effect either permanent sterility (e.g. sectioning and ligation of the Fallopian tubes or the vas deferens) or reversible sterility (e.g. hormonal contraceptives, such as the "birth control pill", intrauterine devices, the cervical diaphragm or vaginal creams, foams and suppositories). However, such means are either not sufficiently effective in inducing sterility, or have a number of undesirable associated side effects. Permanent sterility may be undesirable to many men and women. At present, no consistently effective reversible method of sterilization is available to the male.

Vasectomy (i.e. sectioning and ligation of the vas deferens) has gained popularity in recent years. However, the procedure is generally considered to be irreversible. Thus, vasectomy is not universally desirable.

Although a number of allegedly reversible vas deferens occlusion devices and methods have been proposed, these are generally not reliable. In most cases, such procedures do not completely prevent sperm passage through the vas deferens, and/or are not consistently reversible. Some prior occlusion devices are complicated in design, or tend to result in irreversible damage to the vas deferens during implantation. Some methods require complete sectioning of the vas deferens, which seriously lessens the chances for successful reversal.

Some prior occlusion devices are inflexible, and thus tend to result in injury to the vas deferens and nearby organs during exercise.

Still other devices result in permanent adhesion or other attachment of the device to the vas deferens so that the functional activity of the vas deferens is permanently altered. This in turn decreases the probability of successful reversal of the sterilization procedure.

One prior intravasal occlusion device and method is described in Lee U.S. Pat. No. 3,589,355. The device described in the Lee patent comprises a single intravasal plug with a filiform thread attached to one of its ends. The plug is introduced to the vas by means of a needle, with the thread extending through the vas wall. The thread is then tied around the vas in order to hold the plug in place.

However, is has been reported that the device and method of the Lee patent are not fully effective in blocking the passage of sperm through the vas deferens. Further, ligature of the vas deferens by the Lee method has a strong tendency to damage the vas, with the result in some cases of irreversible sterilization.

SUMMARY OF THE INVENTION

It is an object of the invention to overcome one or more of the problems set forth above.

According to the present invention, a method and device for reversibly occluding a body duct, such as the vas deferens or Fallopian tubes, is provided. The device is simple in construction and is readily surgically implantable. Neither implantation nor the continued presence of the device in the body duct alters the histology of the vas.

As applied to occlusion of the vas deferens, the invention provides substantially complete sterilization of the patient (i.e. no sperm is present in the patient's ejaculate), and such sterilization may be reversed in substantially all cases by simple removal of the device.

According to the method of the present invention, the body duct is blocked at two axially spaced positions without sectioning of the duct by insertion into the duct lumen two plugs of soft, flexible, biocompatible material. The plugs are preferably elongate, and are of substantially luminal cross sectional size at the time of implantation and are connected by a flexible connecting member, such as a suture or other filament, for example.

The plugs are inserted into the duct lumen through the duct wall. Preferably, the major portion of the connecting member extending between the plugs is retained externally of the duct to prevent migration of the plugs, and to aid in subsequent removal of the device.

In a preferred embodiment of the invention, the portion of the body duct retaining the plugs is loosely wrapped with body tissue in order to prevent dilation of the duct around the plugs.

Removal of the device from the duct is readily accomplished by exposure of the duct, removal of the tissue wrap, if present, and incision or puncture of the duct followed by withdrawal of the plugs through the incision or puncture. The incision or puncture in the duct then closes spontaneously, or is closed surgically, as by suturing.

Other objects and advantages of the invention will be apparent to those skilled in the art from the following detailed description, taken in conjunction with the drawings and the appended claims.

BRIEF DESCRIPTION OF THE DRAWINGS

FIG. 1 is a perspective view, taken partially in section, of one embodiment of the occlusive device of the invention;

FIG. 2 is a cross sectional view of the device of FIG. 1 taken generally along line 2—2 of FIG. 1;

FIG. 3 is a perspective view, taken partially in section, of a modified form of the device of FIG. 1;

FIG. 4 is a perspective view, taken partially in section, of an exposed body duct being prepared for insertion of the occlusive device of the invention;

FIG. 5 is a perspective view, taken partially in section, of the duct of FIG. 4 during insertion of the occlusive device of the invention;

FIG. 6 is a perspective view, taken partially in section, of the body duct of FIG. 4 with the occlusive device of the invention in place;

DETAILED DESCRIPTION OF THE INVENTION

Figure 7:
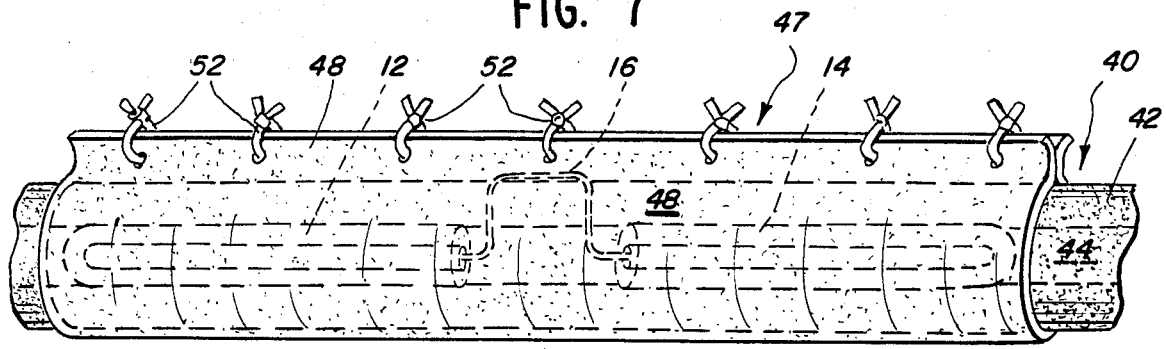
FIG. 7 is a perspective view similar to FIG. 6 showing a body tissue wrapped and sutured about the body duct and occlusive device; and, FIGS. 8 and 9 illustrate removal of the occlusive device of the invention from the body duct of FIGS. 4–7.

Referring to FIGS. 1 and 2, a preferred embodiment of a device 10 for reversibly occluding the lumen of a body duct is illustrated. The device 10 comprises first and second plug elements 12 and 14, respectively, connected by a flexible connecting element 16 securely attached to and extending axially between the plugs 12 and 14.

Each plug 12 and 14 is preferably a generally elongate cylindrical body with an outer diameter x selected to fit snugly within the lumen of a body duct at the time of implantation, without exerting excessive pressure therein. Excessive pressure is pressure sufficient to cause irreversible damage to the wall of the body duct resulting in impairment of functional activity. The outer diameter should not be so large as to result in excessive resistance to insertion into the duct lumen, as described below.

Each plug 12 and 14 has a closed distal end 20, which is preferably tapered to aid in implantation in the body duct. The plugs 12 and 14 of FIG. 1 are hollow, with an internal bore 21 extending longitudinally through the plug 12 or 14 to a proximal end 22 of each plug to define a tool-receiving opening 23. The plugs 12 and 14 may be solid, if desired. Preferably, the proximal end 22 of each plug 12 and 14 is blunt, as shown in FIG. 1, to define a base.

The plugs 12 and 14, and the connecting element 16, are of biocompatible materials. The term "biocompatible" denotes materials which do not promote adverse responses from body tissue.

The plugs 12 and 14 may be of any soft, flexible biocompatible material. For example, Silastic ® and Teflon ® are suitable materials, as are ethylene-vinyl acetate copolymers. Other plastics may also be suitable. Silastic ® (a trademark of Dow Corning Corporation) materials, which contain organosilicon polymers, are especially preferred.

The plugs 12 and 14 may be manufactured by molding, extrusion or other suitable manufacturing processes.

The plugs 12 and 14 are preferably smooth and nonporous. As is known in the art, some porous materials promote invasive tissue growth from a duct wall into the material. If reversibility of an implantation procedure according to the invention is not desired, the plugs 12 and 14 may be of such material as allows tissue ingrowth.

The connecting element 16 preferably comprises a thread, suture or other filament of plastic, nylon, silk or other biocompatible, implantable material. The connecting element 16 is securely attached to each plug 12 and 14 or, if desired, may be integral therewith and may be, but not necessarily, of the same material as the plugs 12 and 14. In the embodiment of FIG. 1, the connecting element 16 is a filament which terminates at its respective ends in knots 24 near the end 20 of each plug so as to resist detachment therefrom. Other means of attaching the connecting element 16 to the plugs 12 and 14 include, for example, looping the connecting element around the plug elements, with or without transection thereof, incorporating the ends 24 of the connecting element in the material of the plugs 12 and 14, or anchoring the ends 24 to the base 22 of each plug 12 or 14.

The connecting element 16 need not comprise a single element, but may comprise separate elements attached to each plug, respectively, to be attached to each other after implantation of the plugs.

The dimensions of the device 10 and the component elements 12, 14 and 16 will depend upon the dimensions of the body duct to be occluded. Each plug 12 and 14 is preferably, but not necessarily, generally cylindrical in shape with an outer diameter x (FIG. 2) of substantially luminal dimension at the time of implantation. Elongation of the plugs 12 and 14 is not critical and there is no minimum length/diameter (i.e. y/x) ratio required. However, it is preferred that the plugs 12 and 14 be generally elongate.

Those skilled in the art will recognize, in the case of the vas deferens, that the diameter of the vas lumen is normally small, but varies depending upon the state of the vas. According to the invention, the size of the plugs 12 and 14 is selected so that the vas lumen flexes snugly about the plugs upon implantation.

For application in occluding the vas deferens, each plug element 12 or 14 has a length y between about 0.5 and 10 centimeters, with a length of about 2–5 centimeters preferred, and an outer diameter x of between about 0.2 and 8 millimeters, with 0.5 to 2.5 millimeters preferred. The connecting element 16 preferably comprises a suture of size No. 1-0 to 6-0, with size No. 4-0 to 5-0 preferred. The spacing z between the bases 22 of the respective plugs 12 and 14 will be from 0.5 to 10 centimeters, with a spacing of 1–2 centimeters preferred. The preferred dimensions refer to use of the device 10 in humans.

If desired, the end 20 of each plug may comprise a relatively hard material such as metal, plastic or an alloy to aid passage of the plug into the body duct, as described below. Referring to FIG. 3, an alternative embodiment of the device 10 includes an insertion probe 30 secured to and extending axially from the end 20 of the plug 12 or 14. The probe 30 comprises a blunt needle which can be removed from the plug end 20 after insertion of the plug into the body duct by puncturing the wall of the duct with the probe 30 and detachment thereof from the plug, as by pulling.

Referring now to FIGS. 4–6, a method of occluding a body duct, such as the vas deferens, by surgical implantation of the occlusion device 10 is described. In FIGS. 4–6, a body duct, generally designated 40, comprises an annular duct wall 42 which defines a lumen 44 extending axially therethrough. Illustratively, the duct 40 is the vas deferens and the lumen 44 is the vas lumen. The wall 42 comprises the vas musculature.

According to the inventive method, at least one, and preferably two apertures, such as puncture holes 46, 46', are formed in the duct wall 42, and as by puncture with a microtool or needle 50. If two holes are formed, the distance between the holes is slightly shorter than the interplug spacing z of FIG. 1.

Referring to FIG. 5, in which the diameter of the holes 46, 46' is exaggerated for clarity, implantation of the occlusive device 10 into the duct lumen 44 is illustrated. Each plug 12 and 14 is inserted into the lumen 44 via a respective hole 46, 46'. Preferably, with hollow plugs 12 and 14, a rigid metal stylus 52 is inserted through the tool-receiving opening 23 and into the bore 21 of each plug to render the plug temporarily rigid for ease of insertion.

The tapered end 20 of each plug is inserted through a respective hole 46, 46' and the plugs are pushed into the lumen 44. Of course, the diameter of each hole 46, 46' dilates to accomodate the respective plugs 12 and 14. After each plug 12 and 14 is received into the lumen 44, as shown in FIG. 6, the blunt base 22 of each plug 12 and 14 resists escape through the respective holes 46, 46'.

It will be appreciated that each hole 46, 46' is so small that it closes automatically about the connecting element 16 after insertion of the plugs 12 and 14, preventing leakage of the contents of the duct. Furthermore, blood vessels, duct musculature, nerves, etc. are not irreversibly damaged. If an incision is used for insertion of the plugs, it should be surgically closed after insertion, as by suturing.

Again with reference to FIG. 6, the flexible connecting element 16 preferably extends between each plug 12 and 14, through the vas wall via the respective holes 46 and 46', with a major portion of the connecting element 16 remaining external to the duct 40 to prevent migration and limit spacing of the plugs 12 and 14. If desired, a flexible sheath (not shown) may be disposed about the interplug length z of the connector 16 in order to prevent cutting of the duct wall 42 by the connector 16.

If desired, a single hole 46, 46' may be utilized. In such a case, the connecting elements 16 forms a loop externally of the duct 40. Further, if desired, the entire device 10 may be disposed within the duct lumen 44.

Referring now to FIG. 7, a preferred embodiment of the invention is shown. As an additional precaution against passage of duct contents about the plugs 12 and 14, a wrapping 47 may be applied about the portion of the duct 40 retaining the plugs 12 and 14 in order to prevent dilation of the duct wall 42 around either of the plugs 12 or 14.

It has been found that wrappings of some synthetic materials, such as Dacron, for example, cause necrosis of body ducts. Therefore, the wrapping should preferably be of body tissue but can be of another material that does no cause necrosis of body tissue.

In the case of occlusion of the vas deferens, a portion of the spermatic fascia 48 from the spermatic cord which is situated closely to the vas deferens 40 may be used to surround the vas deferens. The tissue 48 can be wrapped rather loosely about the vas deferens and the external connecting element 16, and sutured in place, as at points 52 of FIG. 7.

Figure 8:
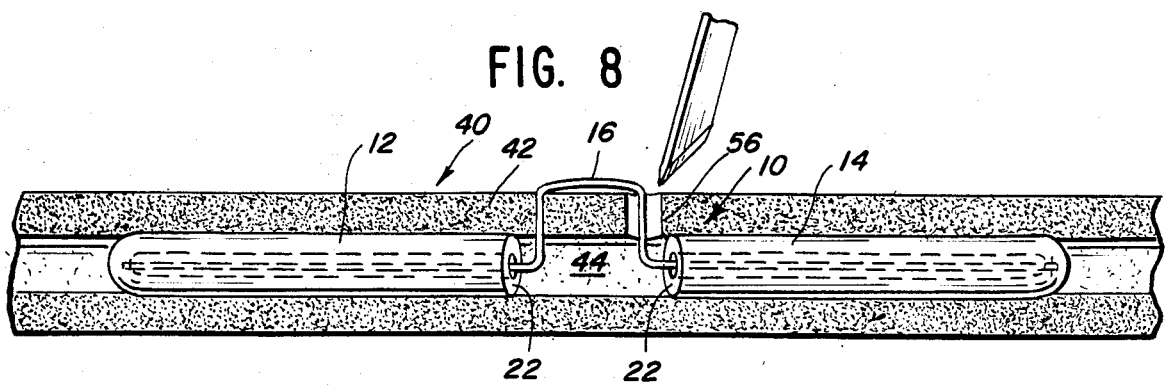
Figure 9:
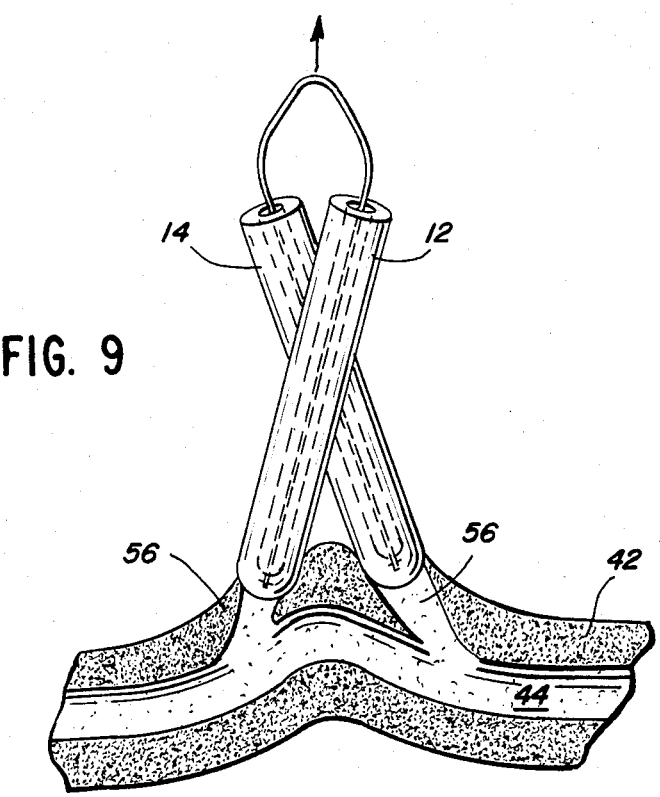

Referring to FIGS. 8 and 9, removal of the occlusive device 10 from the vas deferens 40 is easily accomplished by means of an incision or puncture 56 through the vas wall 42 at each point at which the flexible connecting element 16 extends through the wall 42. The incision should be just large enough to accomodate the base 22 or each plug 12 or 14, which may be removed from the lumen 44 by pulling the connecting element 16, with or without the aid of a forceps or other pulling tool. After removal of the device 10, the holes 56 may require closure, as by sutures.

It will be readily appreciated that the inventive device and method provides means for reversibly occluding a body duct without irreversibly altering the functional activity of the duct. Specifically, a method for occlusion of the vas deferens, thus providing sterilization of a male patient, is provided without damage to the vas which might render the procedure irreversible. Further, since all parts of the device are flexible, the chances of inflicting trauma to the vas deferens due to scrotal movements are minimized.

The method of implantation and removal are simple, and result in minimal trauma. Further, since the device is held in place without ligature, constriction or other damage to blood vessels and other tissues are avoided.

EXAMPLE

The occlusive device 10 of FIGS. 1 and 2 was implanted in the right and left vas deferens in each of six mature Rhesus Macaque (*Macaca arctorides*) male monkeys, according to the procedure shown in FIGS. 4–6 and described above. Tissue wraps were applied as in FIG. 7 in all but one animal.

The sizes of the plugs 12 and 14 are given in Table 2, below. The typical base-to-base spacing z was about 30 mm, with about 20 mm of suture 16 retained externally of the vas. The material of construction of the plugs 12 and 14 was Silastic ®, with a suture connector 16.

Before implantation, the monkeys were ejaculated to establish that their semen contained normal amounts of live spermatozoa. Ejaculation was effected by electroejaculation, as follows: A plastic probe having two metal strips along its length was placed in each animal's rectum. An electrical stimulus (up to 85 mA) was supplied by a power source to the animal via the probe in slowly increasing amounts until ejaculation occurred.

Ejaculate was collected in test tube and immediately checked for sperm motility and forward progression. Motility is defined as the percentage of spermatozoa which have any type of motion. This is a subjective yet reasonable criterion for determining the viability of ejaculated spermatozoa. Forward progression is also a subjective criterion for semen analysis and refers to those sperm which have motility and generally move in a forward manner.

For example, if a semen sample has a motility of 65%, and of the sperm which have some kind of motion $\frac{3}{4}$ are moving forward, the forward progression value is 3 (0 is lowest and 4 is highest). Forward progression is important since sperm which do not move forward will probably not fertilize an egg.

After all samples had been obtained and checked for motility, forward progression and the presence of a coagulum, sperm counts were performed, as follows. 0.1 ml of sample was added to 0.1 ml of Mucolex (Lerner Labs, Stanford, Conn.) brand fixative in 0.8 ml distilled water. (Mucolex brand fixative kills spermatozoa.) This solution was mixed well and a drop or two placed on a hemocytometer. After about five minutes (sufficient time for sperm to settle into a common microscopic plane) the sperm were counted and their concentration per ml determined.

The occlusion devices were kept in place for at least seven months during which time no spermatozoa appeared in the ejaculate even though the primates were ejaculated every two weeks. One animal produced one sample which contained some dead sperm, but this was soon after implantation, and never occurred again. After removal of the devices all of the animals ejaculated spermatozoa again at normal levels. Thus, a 100% success rate was obtained in reversibly obstructing sperm flow though the vas deferens. No vas pathology or alteration of tissues was observed at the time of device removal.

The results of the foregoing testing are described in Tables 1 and 2 below.

TABLE 1

| | Pre-Implantation Semen Analyses* | | | | |
|---|---|---|---|---|---|
| Animal No. | Volume (ml) | Sperm Conc. ($\times 10^6$/ml) | Sperm Count ($\times 10^6$) | Motility (%) | Forward Progression (0-4) |
| 1 | 0.10 | 115 | 11.5 | 85 | 3 |
| 2 | 0.20 | 150 | 30 | 80 | 3 |
| 3 | 0.10 | 105 | 10.5 | 73 | 3 |
| 4 | 0.30 | 160 | 48 | 70 | 3 |
| 5 | 0.20 | 180 | 36 | 75 | 3 |
| 6 | 0.35 | 195 | 68.3 | 80 | 3 |

*Average values. The primates were ejaculated every 2 weeks.

TABLE 2

| | | Implantation Data and Semen Analyses* | | | | Semen Analyses, Last 2 Ejaculates After Device Removal* | | | | |
|---|---|---|---|---|---|---|---|---|---|---|
| | | Plug | | Length of | Semen Data | | | | | |
| Animal No. | Vas Side | Size (mm) (diameter × length) | Tissue Wrap Applied | Time Implanted (months) | (while both sides had implant) anytime/ml) | Volume (ml) | Sperm Conc. 150 (%) | Sperm Count 52.5 (0-4) | Motility 30 | Forward Progression |
| 1 | Left | 0.7 × 25 | Yes | 7 | | | | | | |
| 1 | Right | 1 × 30 | No | 12 | One sample (3rd ejac.) of dead sperm ($10^5$/ml). Otherwise no sperm | 0.40 | 540 | 216.0 | 35 | 4 |
| | Left | 1 × 25 | No | 7 | | | | | | |
| 2 | Right | 0.7 × 30 | Yes | 11 | No sperm at any time | 0.40 | 750 | 300.0 | 30 | |
| | Left | 0.7 × 25 | Yes | 7 | | | | | | |
| 3 | Right | 0.7 × 25 | Yes | 7 | No sperm at any time | 0.30 | 400 | 120.0 | 30 | |
| | Left | 0.7 × 25 | Yes | 7 | | | | | | |
| 4 | Right | 1 × 25 | Yes | 7 | No sperm at any time | 0.20 | 95 | 9.0 | 0 | |
| | Left | 0.7 × 25 | Yes | 7 | | | | | | |
| 5 | Right | 0.7 × 25 | Yes | 7 | No sperm at any time | 0.40 | 180 | 72.0 | 60 | |
| | Left | 0.7 × 25 | Yes | 7 | | | | | | |
| 6 | Right | 0.7 × 25 | Yes | 7 | No sperm at | 0.35 | 150 | 52.5 | 30 | |

*Average values. The primates were ejaculated every 2 weeks. Five out of the six primates possessed spermatozoa in the first ejaculate after device removal.

The foregoing detailed description is given for clearness of understanding only, and no unnecessary limitations should be inferred therefrom, as modifications within the scope of the invention will be obvious to those skilled in the art.

We claim:

1. A method of occluding the vas deferens, said method comprising the step of blocking the lumen of said vas deferens at a plurality of axially spaced positions by positioning at least two elongated plugs having a diameter substantially equal to the diameter of the lumen within said lumen, with said plugs being connected by a flexible connector extending through at least one aperture in the wall of the vas deferens and secured to and extending between said at least two plugs, with said flexible connector permitting movement of said plugs with respect to each other and maintaining an axial spacing between said plugs to prevent sperm passage through the vas deferens.

2. A method of occluding a body duct having a lumen, said method comprising the step of positioning in said lumen at two axially spaced positions two plugs of substantially luminal cross-sectional dimension to block flow through said lumen, said plugs being connected to each other by flexible connecting means secured to and extending between said plugs, said connecting means extending through two apertures in a wall of said duct intermediate to said plugs, said flexible connecting means comprising a flexible filament attached to each of said plugs, and said plugs being positioned in said lumen such that said filament extends through the wall of said ducts through said two spaced apertures therein, each of said apertures being associated with a respective plug, whereby a portion of said filament extends between said plugs externally of said duct to retain said plugs in their respective positions in said lumen and provides a substantially unoccupied inter-plug space therebetween.

3. The method of claim 2 wherein each of said plugs is positioned in said lumen by insertion through a respective one of said apertures provided in the wall of said duct.

4. A method of obtaining reversible male sterilization by occlusion of the vas deferens to block sperm passage therein, said method comprising the steps of:
   (a) providing in the wall of the vas deferens at least one aperture communicating with the exterior of said vas deferens;
   (b) inserting into said vas deferens through said at least one aperture first and second flexible plugs of substantially luminal cross-sectional size, said plugs being interconnected together by flexible connecting means;
   (c) positioning said first and second plugs in axially spaced-apart relation in said vas deferens, at least a portion of said connecting means extending through said at least one aperture between said plugs externally of said vas deferens after insertion of said plugs such that said plugs are retained in said spaced-apart relation in said vas deferens to provide a substantially unoccupied inter-plug space therebetween to block sperm passage in said vas deferens; and
   (d) removing surgically said first and second plugs from the vas deferens.

5. The method of claim 4 wherein each of said first and second plugs comprises an elongate, generally cylindrical plug member having distal and proximal ends, said respective distal ends of said first and second plugs extending in opposite directions away from each other, and wherein said connecting means comprises a flexible filament secured to each of said plugs and extending axially therebetween.

6. The method of claim 5 wherein the respective distal ends of each of said plug members are generally tapered to permit insertion into said vas deferens and each of said proximal ends are blunt, whereby escape of said plug members from said vas deferens through said aperture is resisted.

7. The method of claim 5 wherein said method is carried out in a human and the length of each of said plug members is between about 0.5 and 10 cm, the diameter of each of said plug members is between about 0.2 and 8 mm, and the length of said filament between said proximal ends of said plug member is between about 0.5 and 10 cm.

8. The method of claim 7 wherein in the preferred length of each of said plug members is between about 2 and 5 cm, the preferred diameter of each of said plug members is between about 0.5 and 2.5 mm, and the preferred length of said filament between said proximal ends of said plug member is between about 1 and 2 cm.

9. A device for reversibly occluding the vas deferens possessing peristaltic-like contractory muscle movement comprising:

two elongated plugs of cross-sectional diameter substantially equal to the inside diameter of the vas deferens and length sufficient to substantially engage the periphery of the interior of the vas deferens over a substantial distance when positioned in the lumen, and connecting means interconnecting said plugs and permitting movement of said plugs within the vas deferens due to peristaltic-like contractory muscle movement with respect to one another while maintaining an axial spacing between said plugs to prevent sperm passage through the vas deferens, said connecting means extending through the wall of the vas deferens at at least one location and being sufficiently flexible without functionally traumatizing the vas deferens such that said device, after implantation in the vas deferens, may be removed therefrom to provide a reversible male sterilization procedure.

10. The device of claim 9 wherein said connecting means comprises a filament secured to and extending axially between said plugs.

11. The device of claim 9 wherein each of said plugs has a tapered end and a blunt base, the respective blunt bases facing each other when said plugs are interconnected and positioned within the vas deferens.

12. The device of claim 11 wherein each of said plugs includes an elongated tool-receiving hollow opening to said blunt end.

13. The device of claim 11 wherein each of said plugs includes a blunt needle extending axially from, detachably secured to and mounted on said tapered end.

14. The device of claim 11 wherein each of said plugs has a length of between about 0.5 and 10 cm and a diameter between about 0.2 and 8 mm, and said bases are spaced from each other by between about 0.5 and 10 cm.

15. The device of claim 14 wherein the preferred length of each said plugs length is between about 2 and 5 cm, the preferred diameter of each said plugs is between about 0.5 and 2.5 mm, and the preferred interbase spacing is between about 1 and 2 cm.

16. The device of claim 9 wherein said device is comprised of a smooth, flexible, non-porous material.

17. A device for occluding a vas deferens comprising:
at least two elongated plugs each of soft flexible material and of cross-sectional diameter and length sufficient to substantially engage the periphery of the lumen of the vas deferens over a substantial distance sufficient to block the lumen against the passage of sperm when positioned in the lumen, tool receiving means in each of said plugs defined by an elongated hollow in each of said plugs terminating in a tool receiving opening at one end of each of said plugs, and a thin, flexible filament interconnecting said plugs wherein upon the insertion of each of said at least two plugs into the vas deferens, the cross-sectional diameter is substantially equal to the interior diameter of the vas deferens and said filament permits relative movement of said at least two plugs with respect to each other due to the peristaltic-like contractory muscle movement of the vas deferens while maintaining an axial spacing between each of said at least two plugs to provide occlusion of the vas deferens.

18. The device of claim 17 wherein said filament has a flexibility at least equal to that of No. 4-0 suture.

* * * * *